(12) United States Patent
Aswatha Narayana et al.

(10) Patent No.: US 12,262,867 B2
(45) Date of Patent: Apr. 1, 2025

(54) GRIPS FOR MEDICAL DEVICES

(71) Applicant: Boston Scientific Medical Device Limited, Galway (IE)

(72) Inventors: Balaji Aswatha Narayana, Karnataka (IN); Jeff Insull, Northborough, MA (US); Vijay Kshatriya, Haryana (IN)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 0 days.

(21) Appl. No.: 18/062,357

(22) Filed: Dec. 6, 2022

(65) Prior Publication Data
US 2023/0096513 A1 Mar. 30, 2023

Related U.S. Application Data

(63) Continuation of application No. 16/844,396, filed on Apr. 9, 2020, now Pat. No. 11,547,274.

(60) Provisional application No. 62/832,595, filed on Apr. 11, 2019.

(51) Int. Cl.
*A61B 1/00* (2006.01)
*B25G 1/10* (2006.01)

(52) U.S. Cl.
CPC ...... *A61B 1/00066* (2013.01); *A61B 1/00105* (2013.01); *A61B 1/0014* (2013.01); *B25G 1/102* (2013.01)

(58) Field of Classification Search
CPC ............ A61B 1/00066; A61B 1/00105; A61B 1/0014; B25G 1/102
See application file for complete search history.

(56) References Cited

U.S. PATENT DOCUMENTS

| | | | |
|---|---|---|---|
| 4,785,495 A * | 11/1988 | Dellis | B29C 37/0053 264/222 |
| 5,353,474 A | 10/1994 | Good et al. | |
| 6,082,468 A * | 7/2000 | Pusateri | B25F 5/02 173/171 |
| 6,083,151 A | 7/2000 | Renner et al. | |

(Continued)

FOREIGN PATENT DOCUMENTS

| | | |
|---|---|---|
| DE | 10 2015 113426 A1 | 2/2017 |
| JP | 2004358011 A | 12/2004 |

(Continued)

OTHER PUBLICATIONS

International Search Report and Written Opinion of the International Search Authority dated Sep. 18, 2020, issued in corresponding International Application No. PCT/IB2020/000391, filed Apr. 9, 2020 (66 pages).

*Primary Examiner* — Aaron B Fairchild
(74) *Attorney, Agent, or Firm* — Bookoff McAndrews, PLLC (57) ABSTRACT

According to one aspect, a hand assist device may be configured for use with an endoscope. The hand assist device may comprise a body configured to removably couple to a handle of the endoscope. The body may comprise a recess configured to receive the handle of the endoscope. The recess may extend from a proximal end of the body to a distal end of the body. The body may also comprise a palm support portion and a finger support portion proximal to the palm support portion. The body may further comprise a base support portion distal to the palm support portion.

20 Claims, 9 Drawing Sheets

(56) References Cited

U.S. PATENT DOCUMENTS

| | | |
|---|---|---|
| 8,092,373 B1 | 1/2012 | Papouras et al. |
| 2004/0015050 A1 | 1/2004 | Goto et al. |
| 2008/0249370 A1 | 10/2008 | Birnkrant et al. |
| 2010/0081874 A1 | 4/2010 | Miyamoto et al. |
| 2013/0267777 A1 | 10/2013 | Avitsian et al. |
| 2017/0007100 A1 | 1/2017 | Dejima |

FOREIGN PATENT DOCUMENTS

| | | |
|---|---|---|
| JP | 2005-230183 A | 9/2005 |
| JP | 2006-068550 A | 3/2006 |
| JP | 2006-212048 A | 8/2006 |
| JP | 2007275154 A | 10/2007 |
| JP | 2011069883 A | 4/2011 |

* cited by examiner

*FIG. 10*

GRIPS FOR MEDICAL DEVICES

CROSS-REFERENCE TO RELATED APPLICATIONS

This application is a continuation of U.S. application Ser. No. 16/844,396, filed Apr. 9, 2020, which claims the benefit of priority from U.S. Provisional Application No. 62/832,595, filed Apr. 11, 2019, each of which is incorporated by reference herein in its entirety.

TECHNICAL FIELD

Various aspects of the present disclosure relate generally to grips for handles of medical devices. More specifically, embodiments of the present disclosure relate to add-on grips for use with a handle of an endoscope or other medical device, among other aspects.

BACKGROUND

During endoscopic procedures, the medical professional operating the endoscope often wraps their entire palm around a grip or handle portion of the device. Various actuators on the handle of the endoscope require the medical professional to contort their hands frequently and for prolonged periods of time during a procedure, which can cause strain, or even an injury. In some cases, actuation of different scope controls, like knobs or an elevator, may result in movements of the medical professional's thumb or other fingers, which may result in the loss of gripping power. Endoscope operators can experience wrist and hand discomfort resulting from holding and manipulating the endoscope's handle. In some cases, medical professionals may experience symptoms similar to those of Carpal Tunnel Syndrome or tendonitis. When a medical professional experiences fatigue or other pain in the hand or wrist, the medical professional may shift from a primary grip position to a secondary grip position that may be a less powerful grip than the primary grip position, such as shifting from a four finger grip to a three finger grip.

When a medical professional repeatedly readjusts his or her hand grip in between procedure tasks, the procedure may be prolonged and procedural tasks may be more difficult. Endoscopes and other medical devices with handles that include improved support for the medical professional's hand may help address one or more of these or other issues.

SUMMARY

Aspects of the disclosure relate to, among other things, systems, devices, and methods for assisting a user's hand grip on an endoscope or other medical device. Each of the aspects disclosed herein may include one or more of the features described in connection with any of the other disclosed aspects.

According to one aspect, a hand assist device may be configured for use with an endoscope. The hand assist device may comprise a body configured to removably couple to a handle of the endoscope. The body may comprise a recess configured to receive the handle of the endoscope. The recess may extend from a proximal end of the body to a distal end of the body. The body may also comprise a palm support portion and a finger support portion proximal to the palm support portion. The body may further comprise a base support portion distal to the palm support portion.

In other aspects of the present disclosure, the hand assist device may include one or more of the features below. The body of the hand assist device may define a longitudinal opening between two longitudinal edges of the body and the longitudinal opening may lead to the recess. The palm support portion may be configured to fill a space between a palm and a handle body of an endoscope handle and may include a curved portion that protrudes radially outward from a central longitudinal axis of the body. The curved portion may have an apex at the radially-outermost portion of the body. The finger support portion may be configured to be positioned adjacent to at least one button of the handle when the device is coupled to the endoscope. The finger support portion may be configured to fill a space between an index finger and a handle of the endoscope. The finger support portion may be configured to be proximate to and distal to an end portion of an umbilicus of the endoscope when the device is coupled to a handle of the endoscope. The base support portion may project radially outward from a central longitudinal axis of the body and may be configured to align with the ulnar side of a palm. The base support portion may have a concave exterior surface facing radially away from the central longitudinal axis. The body may comprise a surface protrusion configured to be positioned between a middle finger and a ring finger, and the surface protrusion may be positioned between the palm support portion and the finger support portion. The body may comprise a locking portion configured to receive a medical device. The locking portion may be C-shaped and may define an interior to receive a medical instrument. The locking portion may have a free end separated from a surface of one of the palm support portion or the base support portion. The body may comprise a flexible material such that the recess can be forced between an at-rest configuration and an enlarged configuration for receiving an endoscope.

In other aspects, an endoscope system may comprise an endoscope including a handle. The endoscope system may also comprise a hand assist device coupled to the handle of the endoscope. The hand assist device may comprise a body. The body may comprise a channel configured to receive the handle of the endoscope. The channel may extend from a proximal end of the body to a distal end of the body. The body may also comprise a palm support portion, a finger support portion proximal to the palm support portion, and a base support portion distal to the palm support portion.

In other aspects of the present disclosure, the endoscope system may include one or more of the features below. The body may be a unitary body. The body may further comprise a locking portion configured to receive an accessory device. The channel may taper from the proximal to distal direction.

In other aspects, a method of operating an endoscope that includes a handle is disclosed. The method may include inserting the handle into a recess of a body of a hand assist device to removably attach the endoscope to the hand assist device. The recess may extend along a longitudinal axis from a proximal end of the body to a distal end of the body. The hand assist device may further comprise a palm support portion, a finger support portion proximal to the palm support portion, and a base support portion distal to the palm support portion. The method may further include gripping the palm support portion of the hand assist device to hold the endoscope. In addition, the method may include performing an operation on a patient.

In other aspects of the present disclosure, the method of operating an endoscope system may include one or more of the steps and/or features below. The method may further include at least one of (a) contacting the base support portion with an ulnar side of a palm so that the base support portion supports the ulnar side of the palm and (b) contacting the finger support portion with an index finger during actuation of an actuator of the endoscope. Inserting the handle into the recess may include expanding an opening of the recess. The method may further include removing the handle from the recess after performing the operation.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. Throughout the figures included in this application, arrows labeled "P" and "D" are used to show the proximal and distal directions in the figure. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Further, relative terms such as, for example, "about," "substantially," "approximately," etc., are used to indicate a possible variation of ±10% in a stated numeric value or range.

Embodiments of this disclosure seek to improve a physician's ability to grip, manipulate, and otherwise apply force to a handle of a medical device, such as an endoscope, during a medical procedure and, as a non-limiting exemplary benefit, help reduce the need to reposition a user's hand during a procedure, among other aspects.

Figure 1A:
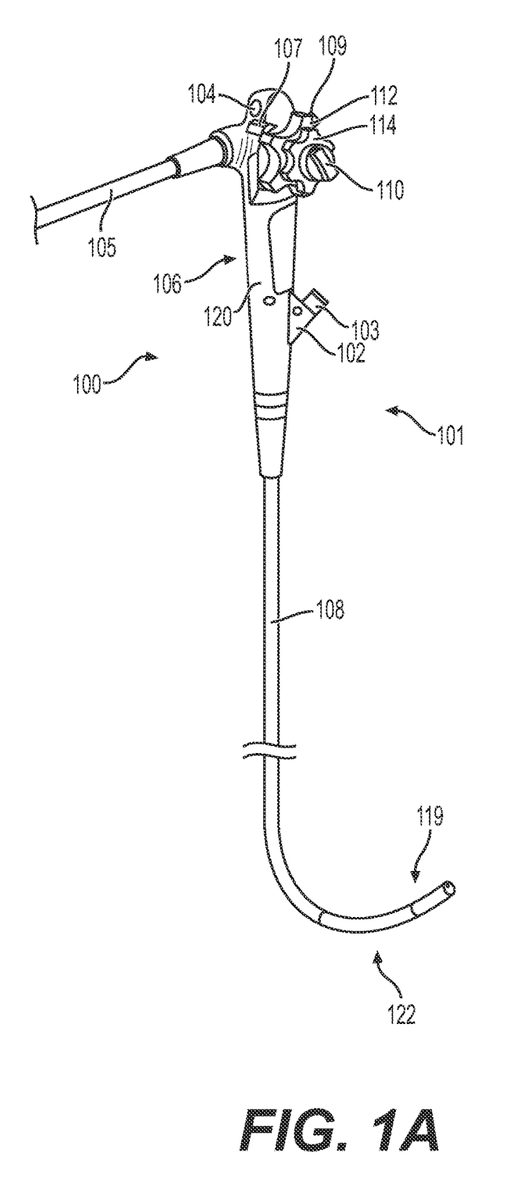
FIGS. 1A and 1B are perspective views of an exemplary endoscope, according to aspects of this disclosure.
Figure 1B:
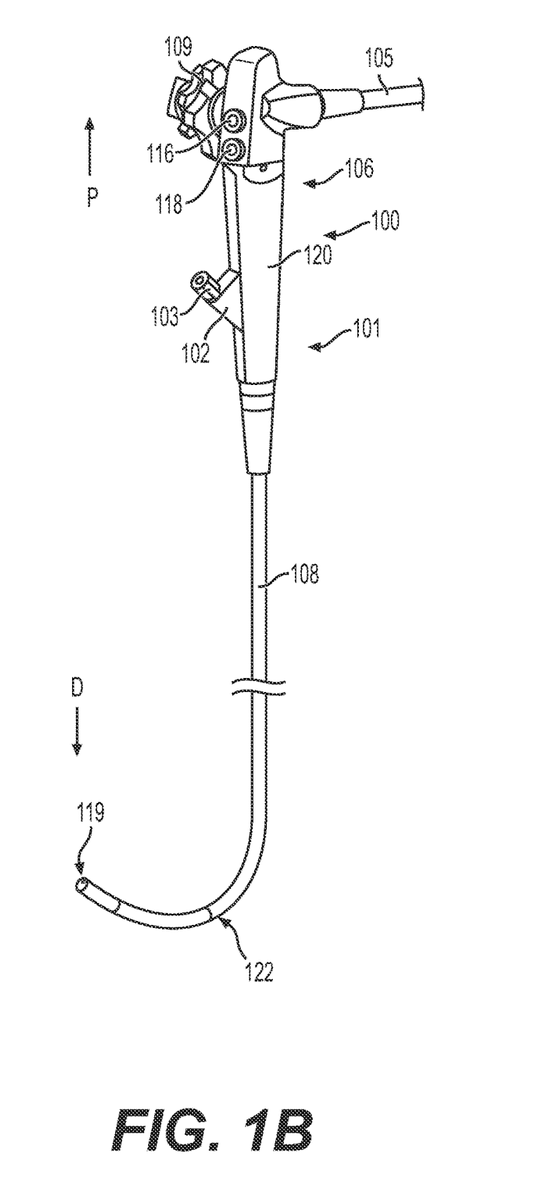

FIGS. 1A and 1B show a perspective view of an exemplary endoscope system 100. Endoscope system 100 may include an endoscope 101. Endoscope 101 may include a handle assembly 106 and a flexible tubular shaft 108. The handle assembly 106 may include a biopsy port 102, a biopsy cap 103, an image capture button 104, an elevator actuator 107, a first locking lever 109, a second locking lever 110, a first control knob 112, a second control knob 114, a suction button 116, an air/water button 118, a handle body 120, and an umbilicus 105. Any of the actuators, elevators, knobs, levers, ports, or caps of endoscope system 100 may serve any purpose and are not limited by any particular use that may be implied by the respective naming of each component used herein. The umbilicus 105 may extend from handle body 120 to auxiliary devices, such as a control unit, water supply, or vacuum source. Shaft 108 may terminate at a distal tip 119. Shaft 108 may include an articulation section 122 for deflecting distal tip 119 in up, down, left, and/or right directions. Handle body 120 may be tapered and may narrow as the handle extends distally such that the profile of the handle body 120 is smaller at its distal end than at its proximal end.

In operating endoscope system 100, a user may use their left hand to hold the handle assembly 106 (shown in FIG. 2A) while the right hand is used to hold accessory devices and/or operate one or more of the actuators of the handle assembly 106, such as the first and second control knobs 112, 114 and the first and second locking levers 109, 110. The user may grasp the handle assembly 106 by wrapping the user's hand around the handle body 120. When grasping handle body 120, the user may use the left thumb to operate the first and second control knobs 112, 114 and the elevator actuator 107 (through rotation about their axis), and may use a left-hand finger to operate the image capture button 104, the suction button 116, and the air/water button 118 (each by pressing).

Figure 2A:
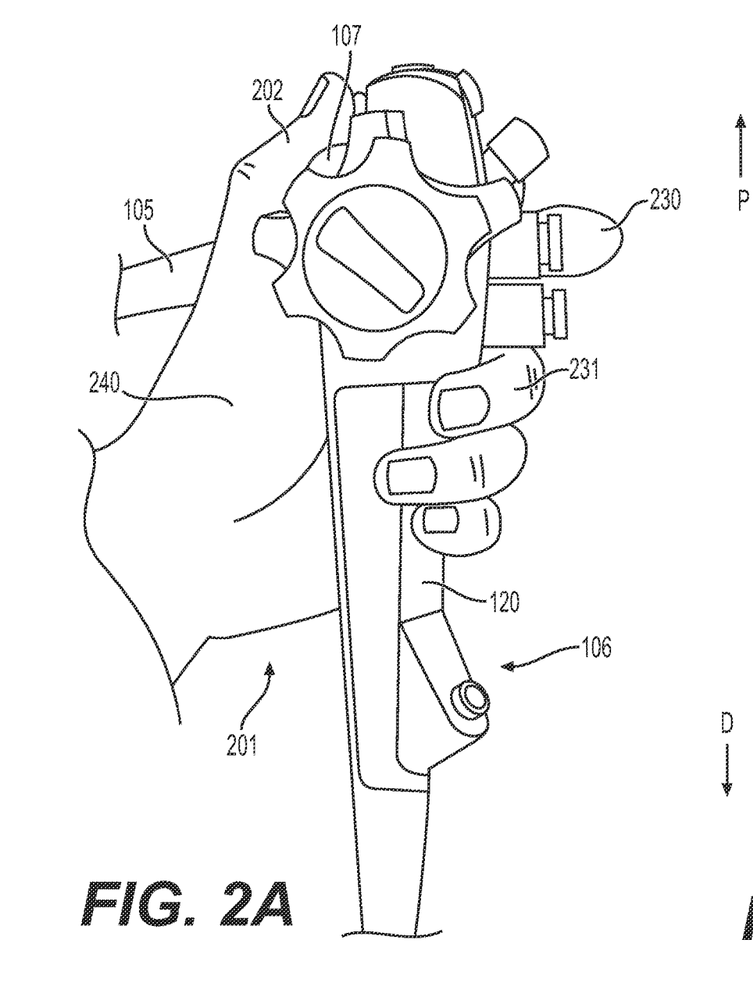
FIGS. 2A and 2B are perspective views of a user's hand holding an endoscope handle, according to aspects of this disclosure.
Figure 2B:
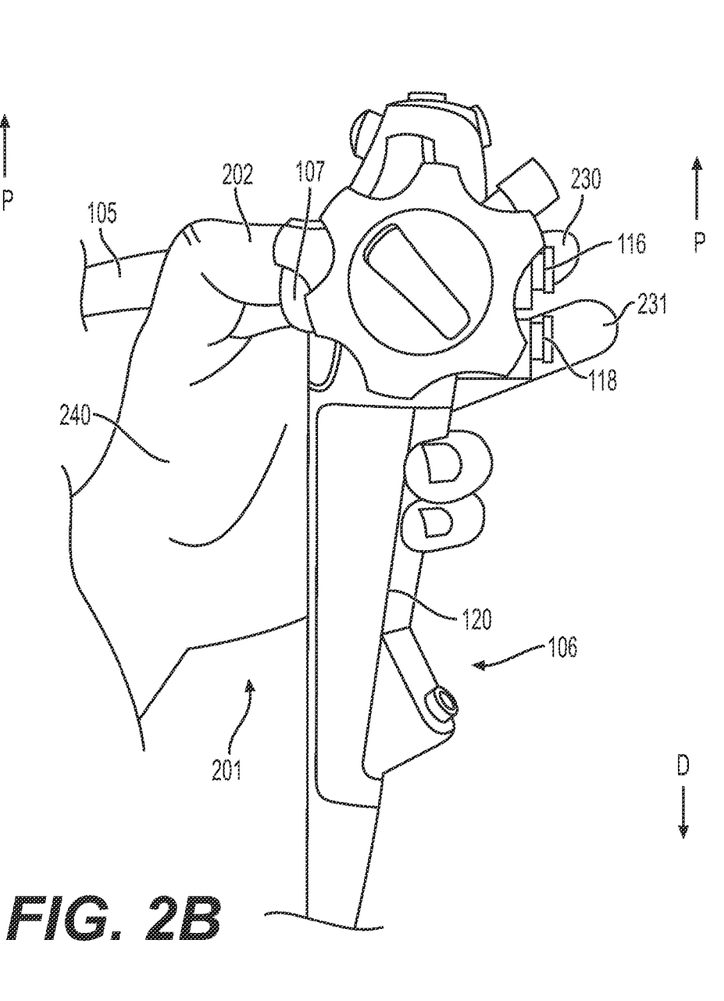

FIGS. 2A and 2B show an exemplary user's left hand 201 grasping handle assembly 106 without a hand assist device. The user's left index finger 230 and middle finger 231 may be used to operate the suction button 116 and the air/water button 118. The user may position the thumb 202 of the grasping hand 201 over the elevator 107 and move the elevator 107 along a circular path from a first position (shown in FIG. 2A) to a second position (shown in FIG. 2B) by moving the thumb 202. As shown in FIG. 2B, the palm 240 may move away from the handle body 120 when the thumb 202 moves from the first position to the second position. A space may be created between a user's palm 240 and handle body 120. When a user's palm 240 moves away from the handle body 120, the user may lose gripping power which may hinder the user's ability to control and move the handle assembly 106.

Figure 3A:
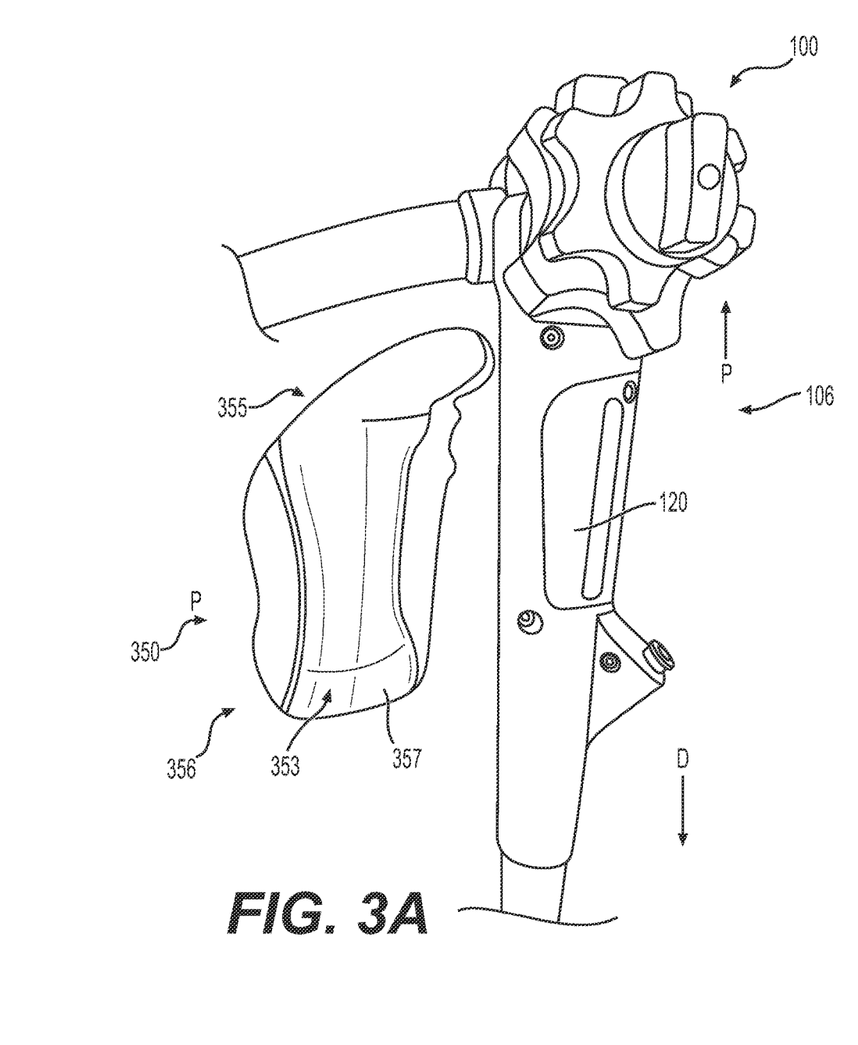
FIGS. 3A and 3B are perspective views of an endoscope handle and a hand assist device, according to aspects of this disclosure.
Figure 3B:
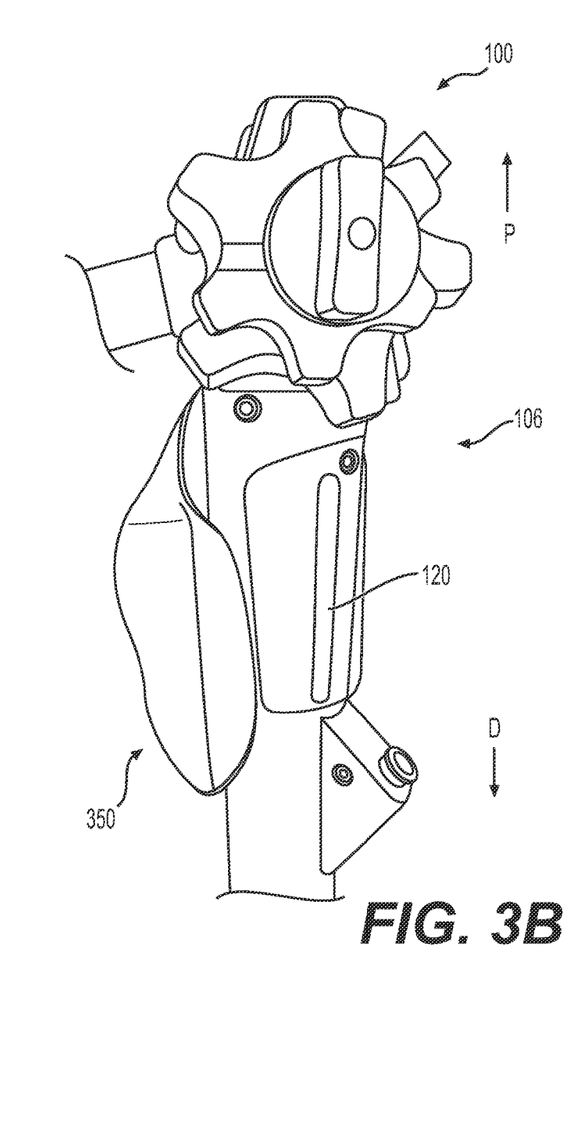

FIG. 3A shows a perspective view of handle assembly 106 and an exemplary hand assist device 350, and FIG. 3B shows a perspective view of the hand assist device 350 coupled to handle assembly 106. Hand assist device 350 may include a channel 353 extending from a proximal end 355 to a distal end 356 of hand assist device 350. In some examples, hand assist device 350 may be removably coupled to handle body 120 by positioning handle body 120 within channel 353, as shown in FIG. 3B. Hand assist device 350 may be made of a soft and/or flexible material such as an elastomer, and may be "clipped on" or "snapped onto" handle body 120, or otherwise coupled to handle body 120 via a friction fit. For example, a user may bend hand assist device 350 to widen channel 353 to allow handle body 120 to be positioned within channel 353. Once handle body 120 is positioned within channel 353, the user may release hand assist device 350 from the bending force, and the inner surface 357 of channel 353 may then move radially inward towards the longitudinal axis of hand assist device and may become flush (or substantially flush) with an exterior surface of handle body 120. A mold used to form inner surface 357 of channel 353 may be the reverse of a mold used to form corresponding portions of handle body 120, so that inner surface 357 is flush with the outer surface of handle body 120. In other examples, hand assist device 350 may be configured to couple to a different style of endoscope handle or any other medical device handle. In some examples, the inner surface 357 of channel 353 may be configured to align with an exterior surface of handle body 120. Inner surface 357 may be a material designed to create friction between the inner surface 357 and handle body 120, which may help prevent the hand assist device 350 from moving when coupled to handle body 120. In some examples, hand assist device may be unitary and/or may be injection molded. Hand assist device may be made of a single material, such as silicone. In some examples, hand assist device may be made of natural rubber, synthetic rubber materials, thermoplastic materials, and/or foam based materials. FIGS. 4A-4D provide more detailed schematics of hand assist device 350.

Figure 4A:
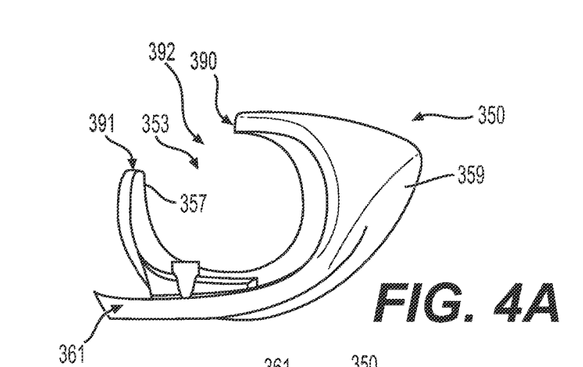
FIGS. 4A-4D are top, front, side, and rear views, respectively, of a hand assist device, according to aspects of this disclosure.
Figures 4B, 4C, 4D:
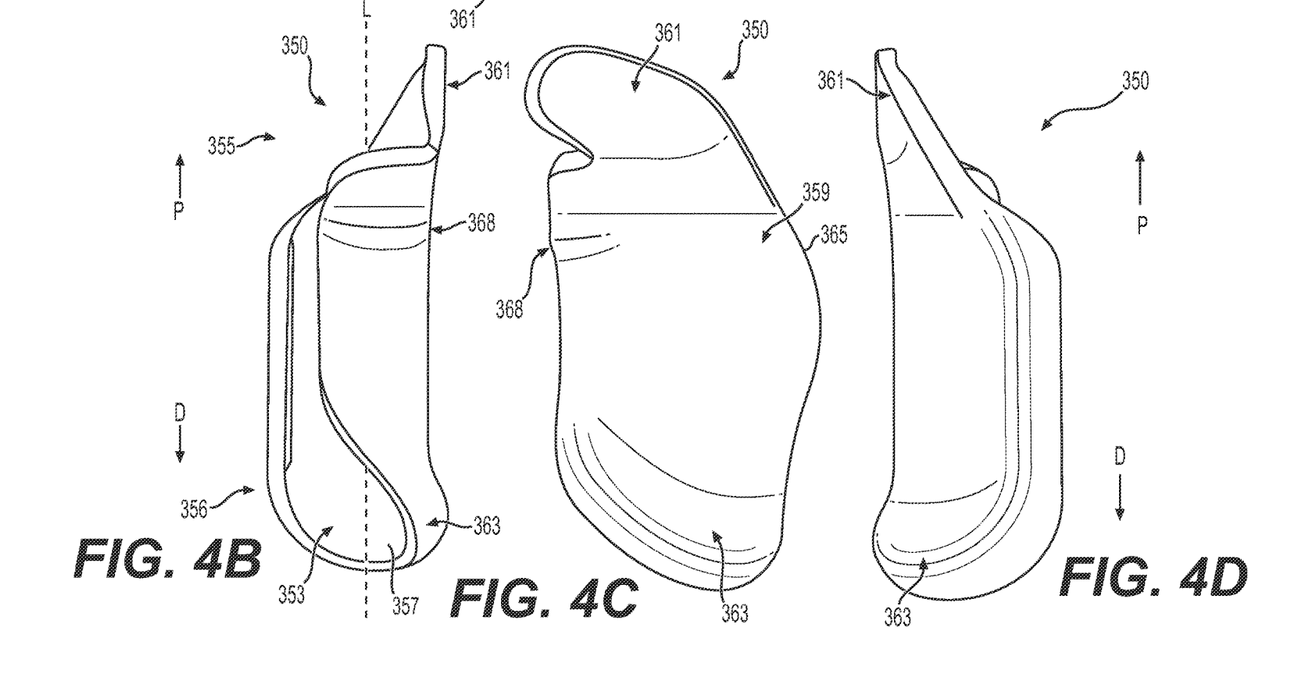

FIGS. 4A-4D show top, front, side, and rear views of hand assist device 350. In some examples, hand assist device 350 may include a palm support portion 359, a finger support portion 361, and a base support portion 363. The inner surface 357 of channel 353 may be curved such that it extends more than half way around the circumference of handle body 120 when hand assist device 350 is coupled to handle body 120. For example, FIG. 4A shows an inner surface 357 that extends approximately 270 degrees around the central longitudinal axis L of hand assist device 350. Hand assist device 350 may be made in any size to fit a variety of user hand sizes. In some examples, hand assist device 350 may include a longitudinal opening 392 between opposing edges 390, 391. Longitudinal opening 392 may lead to channel 353.

Figure 5:
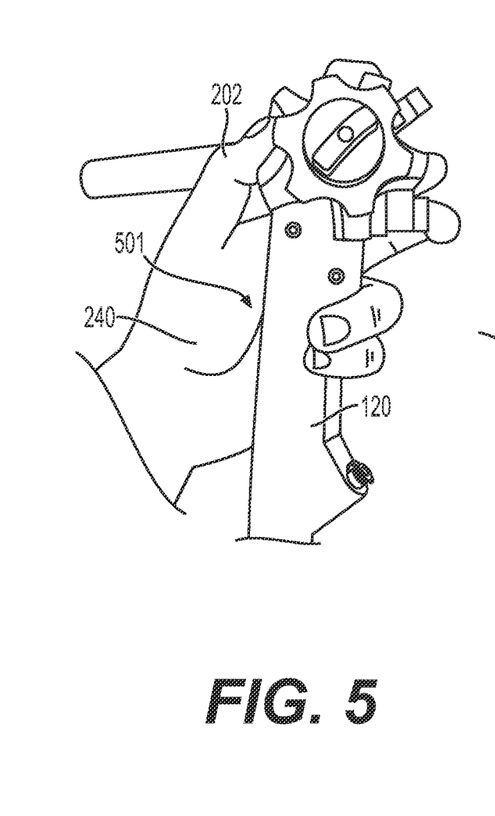
FIG. 5 is a side view of a user's hand holding an endoscope handle, according to aspects of this disclosure.
Figure 6A:
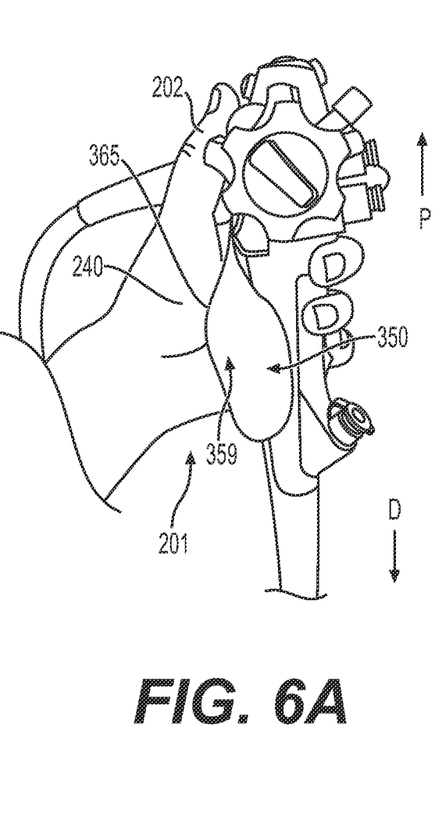
FIGS. 6A and 6B are side views of a user's hand holding an endoscope handle and a hand assist device, according to aspects of this disclosure.
Figure 6B:
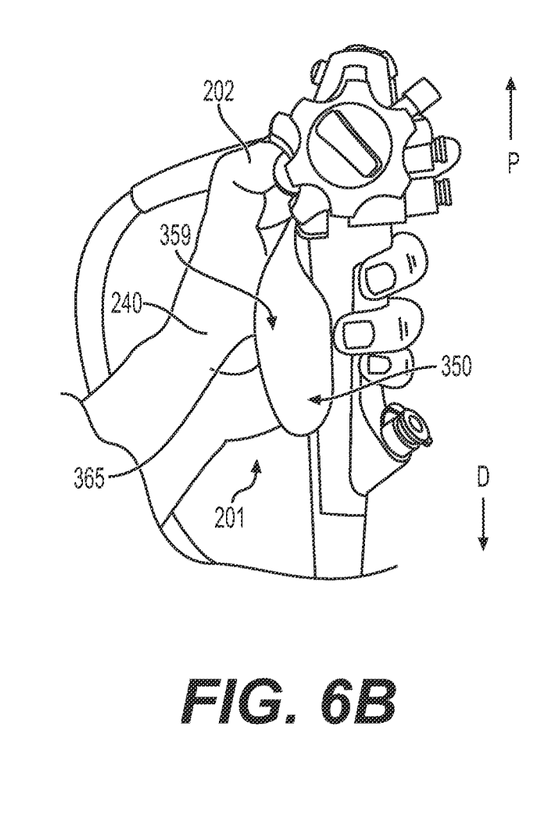

Palm support portion 359 of hand assist device 350 may be configured to consume space 501 (shown in FIG. 5) between the user's palm 240 and a handle body 120 during use of an endoscope 101. In some examples, palm support portion 359 extends radially outward from the longitudinal axis L of hand assist device 350 relative to the distal and proximal ends 355, 356. Palm support portion 359 may have a greater cross-sectional thickness than other portions of device 150, including finger support portion 361, for example. Palm support portion 359 may include a curved protruding portion 365 configured to support a user's palm 240. The curved protruding portion 365 may include an apex at the widest point of hand assist device 350. In some examples, the curved protruding portion 365 may have an apex at the radially-outermost portion of the hand assist device 350. As shown in FIGS. 6A and 6B, palm support portion 359 may contact the user's palm 240 when the user moves elevator 107 from the first position (shown in FIG. 6A) to the second position (shown in FIG. 6B), which may help the user maintain the rip of his or her hand onto handle body 120 when moving elevator 107. By filling the space 501 between the user's palm 240 and handle body 120, palm support portion 359 may help the user maintain a powerful grip during a procedure.

Figure 7:
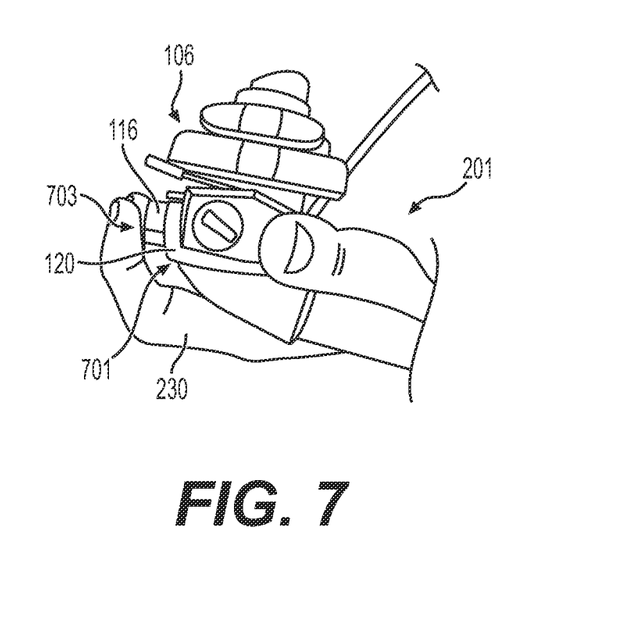
FIG. 7 is a top view of a user's hand holding an endoscope handle, according to aspects of this disclosure.
Figure 8:
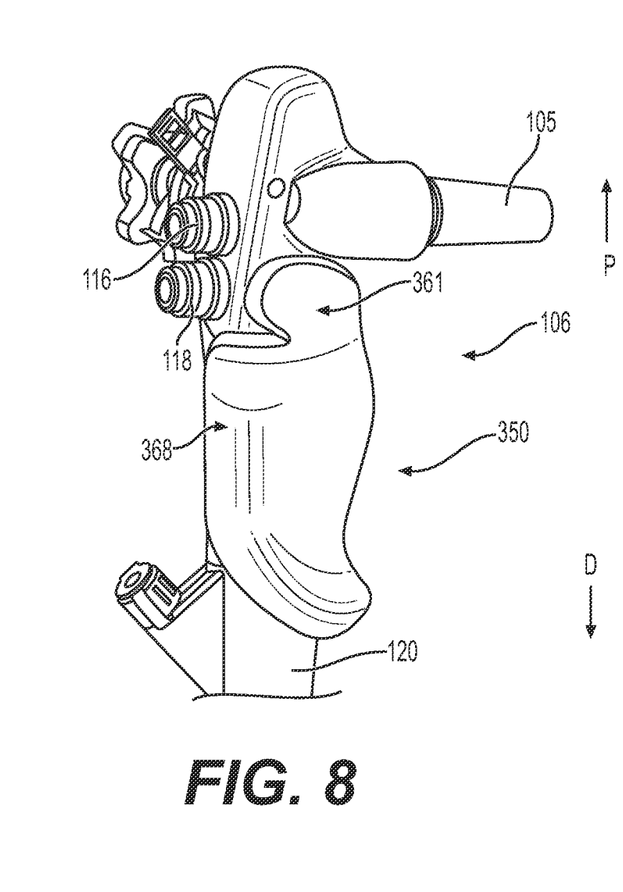
FIG. 8 is a perspective view of an endoscope handle and a hand assist device, according to aspects of this disclosure.

FIG. 7 shows a top view of a user's hand 201 holding handle assembly 106 without a hand assist device 350. A space 701 may be created between a user's index and middle fingers 230, 231 and the handle body 120, when a user actuates the suction button 116 and/or the air/water button 118 of handle assembly 106. Finger support portion 361 may be configured to fill at least some of space 701. In some examples, finger support portion 361 may be at the proximal portion of hand assist device 350 and may protrude radially-outward from, or otherwise be angled relative to, the longitudinal axis L. When hand assist device 350 is coupled to handle assembly 106, finger support portion 361 may be proximate to the suction button 116, the air/water button 118, and the umbilicus 105 (shown in FIG. 8). In some examples, finger support portion 361 may be flush with a surface of handle body 120 on the opposite side of the handle body 120 as the first control knob 112 and the second control knob 114. Finger support portion 361 may be at the proximalmost end of hand assist device 350. By filling at least some of space 701, finger support portion 361 may help the user position a distal phalange portion 703 of their index finger 230 or middle finger 231 proximate to the suction button 116 and/or the air/water button 118. Also, finger support portion 361 may facilitate contact between the inner surface of the user's index and ring fingers and the hand assist device 350, which may facilitate actuation of buttons while maintaining proper grip of handle assembly 106. In addition, finger support portion 361 may help alleviate stress on the user's ring and little fingers when the user actuates the suction button 116 and/or the air/water button 118.

In some examples, hand assist device 350 may include a surface protrusion 368 configured to be positioned between the user's middle and ring fingers when the user is gripping hand assist device 350. Surface protrusion may extend transverse to longitudinal axis L of hand assist device 350, and may be positioned substantially opposite curved protruding portion 365.

Figure 9A:
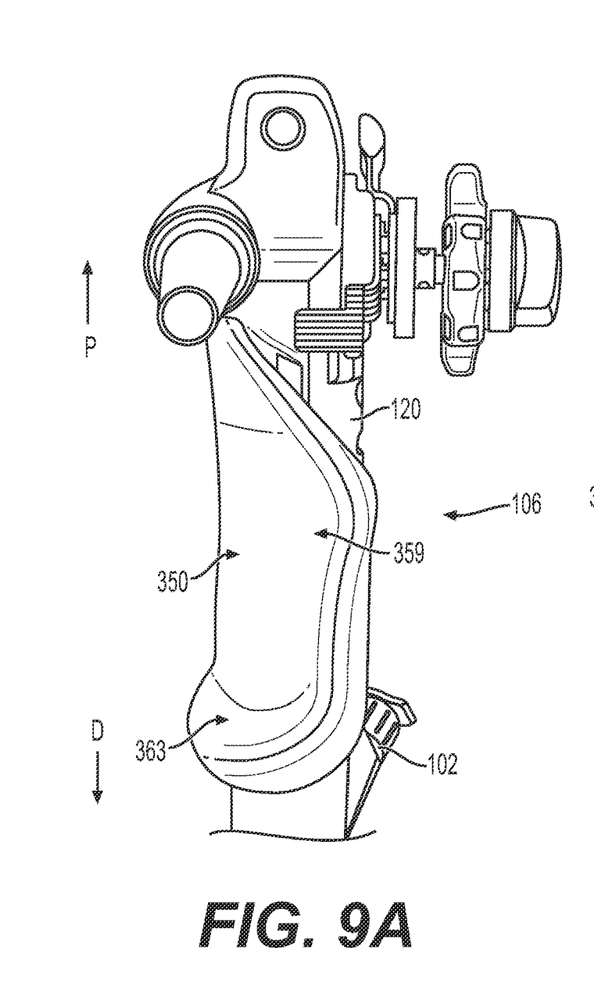
FIG. 9A is a rear view of an endoscope handle and a hand assist device, according to aspects of this disclosure.

Base portion 363 may be at the distal portion 356 of hand assist device 350. In some examples, base portion 363 may be configured to support the bottom of a user's hand, i.e. the portion of the hand that extends from the little finger to the wrist. For example, base portion 363 may be configured to support the ulnar side of the user's palm 240. Base portion 363 may be concave and curve radially outward from a proximal portion of hand assist device 350 and may be configured to align with a bottom edge 910 of a user's hand 201. FIG. 9A shows a rear view of a handle assembly 106 with a hand assist device 350 coupled to handle body 120. When handle assist device 350 is coupled to handle body 120, base portion 363 is proximate to biopsy port 102, on a side of handle body 120 opposite biopsy port 102. In some examples, base portion 363 includes a curved surface that protrudes radially outward from the longitudinal axis L.

Figure 9B:
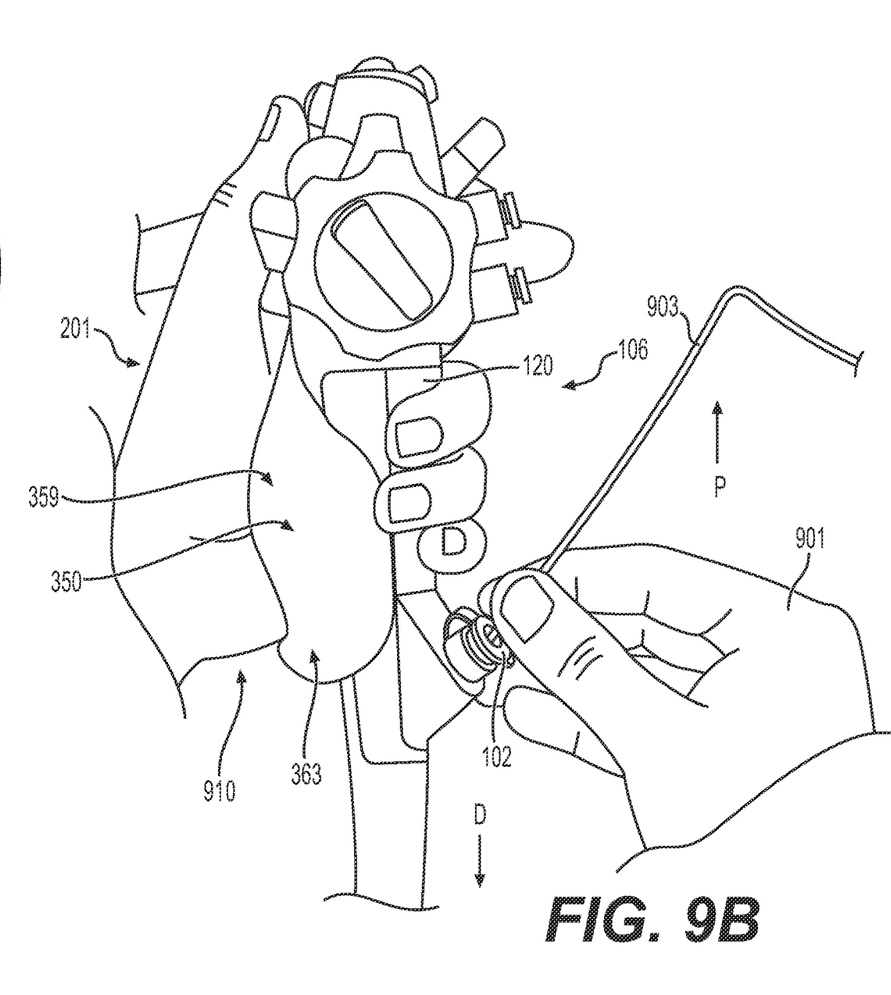
FIG. 9B is a perspective view of a user's left hand holding an endoscope handle and a hand assist device and the user's right hand holding a tool, according to aspects of this disclosure.

FIG. 9B shows a user's left hand 201 holding handle assembly 106 and hand assist device 350 while the user's right hand 901 positions a tool 903 within biopsy port 102. When a user is pulling an accessory 903 out of biopsy port 102, base portion 363 may provide support for the user's left hand 201 when the user pushes in the distal direction with the left hand 201 and/or pulls in the proximal direction with the right hand 901. Thus, base portion 363 may help reduce the effort required to grip handle assembly 106 when removing an accessory 903 from biopsy port 102 and may reduce the number of times a user needs to reposition his or her hand 201.

Figure 10:
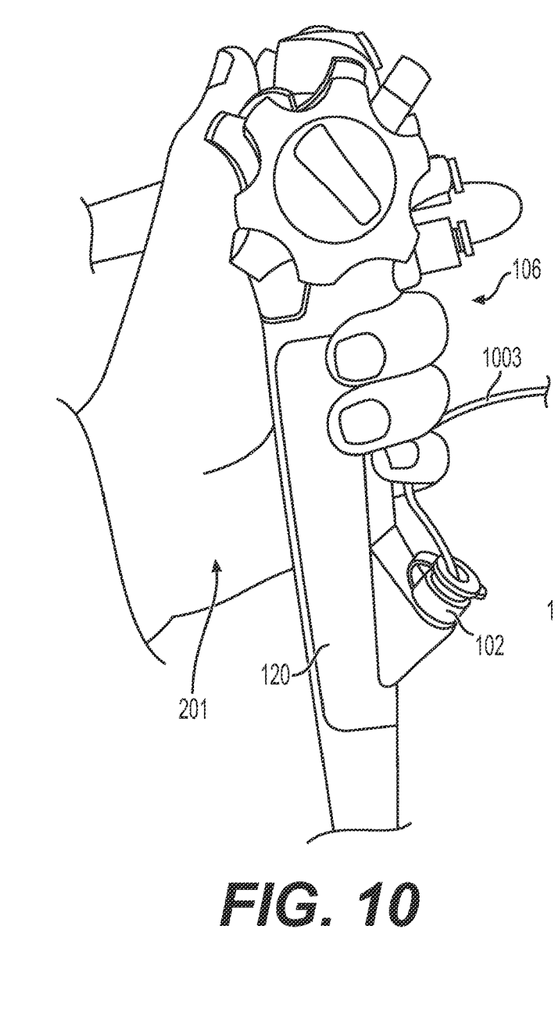
FIG. 10 is a side view of a user's hand holding an endoscope handle and a tool, according to aspects of this disclosure.

FIG. 10 shows a perspective view of a user's hand holding a handle assembly 106 without a hand assist device 350. In FIG. 10, the user's hand 201 is holding accessory 1003 with a little finger. The user may need to hold the accessory 1003 and prevent accessory 1003 from moving within biopsy port 102, for example to prevent the accessory from moving within the endoscope while another medical professional exchange one or more devices on guidewires. When a user is holding an accessory 1003 while gripping handle body 120, the user may experience strain in the left hand 201 due to the awkward positioning of the little finger.

Figure 11A:
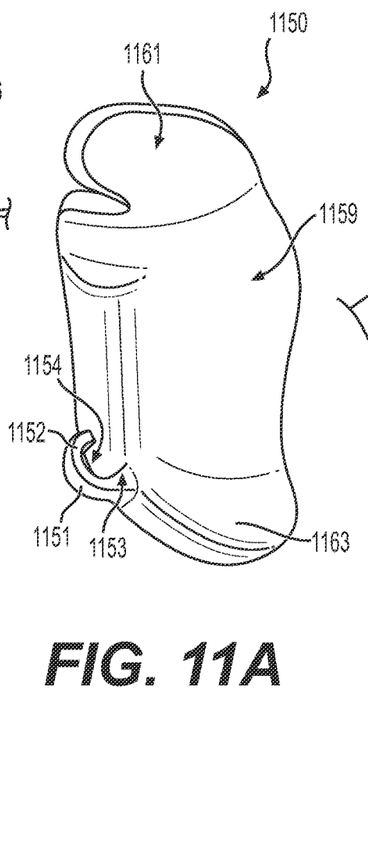
FIG. 11A is a perspective view of a hand assist device, according to aspects of this disclosure.

FIG. 11A shows another embodiment of a hand assist device 1150 including a locking portion 1151. Similar to hand assist device 350, hand assist device 1150 may include a finger support portion 1161, a palm support portion 1159, a base support portion 1163, and any of the features previously described in relation to hand assist device 350. Locking portion 1151 may be C-shaped and may project radially outward from a portion of hand assist device 1150 proximate to or within base portion 1163. Locking portion 1151 may include a distal end 1152 and a proximal end 1153. Distal end 1152 may be free and may be spaced from an exterior surface of hand assist device 1150 to allow an accessory 1003 to pass into an opening 1154 of the locking portion 1151. The C-shaped locking portion 1151 may be positioned such that the proximal and distal ends 1153, 1152 are the portion of the locking mechanism that is closest to the central longitudinal axis of hand assist device 1150. FIGS. 12A-12D show top, front, side, and rear views, respectively, of hand assist device 1150 including locking portion 1151, palm support portion 1159, finger support portion 1161, and base support portion 1163. In other examples, locking portion may be a hook, may be fixed to hand assist device 1150 at both proximal and distal ends, or may be positioned at a proximal portion of hand assist device 1150.

Figure 11B:
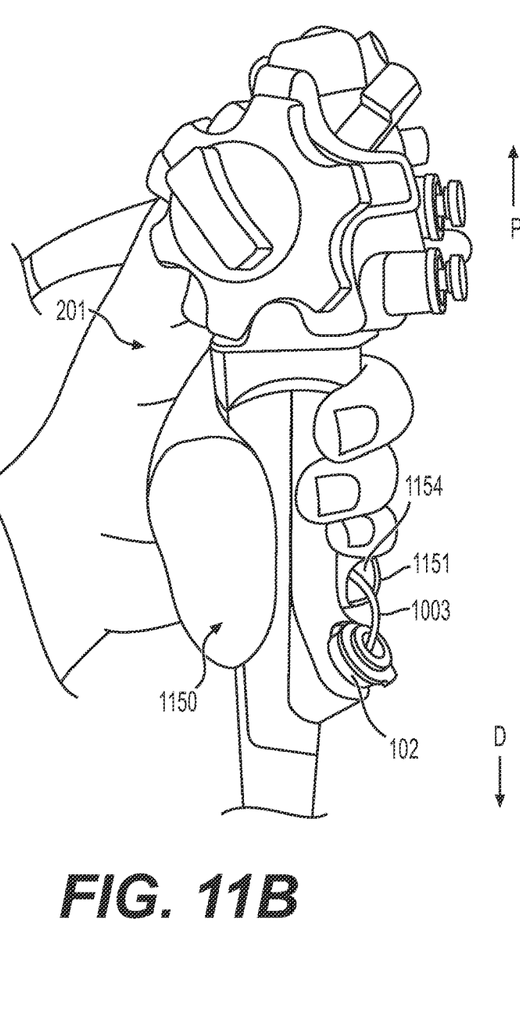
FIG. 11B is a side view of a user's hand holding an endoscope handle and a hand assist device, according to aspects of this disclosure.
Figure 12A:
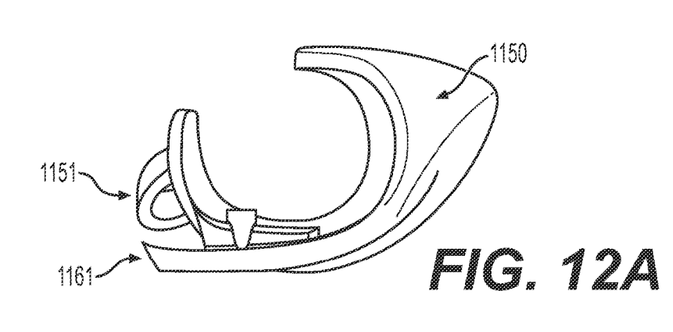
FIGS. 12A-12D are top, rear, side, and front views of a hand assist device, according to aspects of this disclosure.
Figures 12B, 12C:
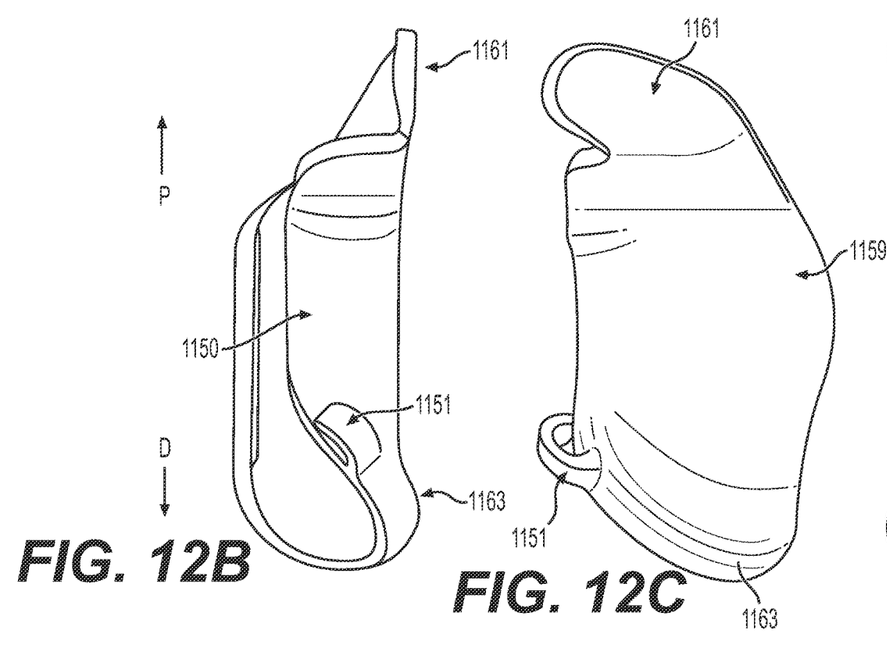
Figure 12D:
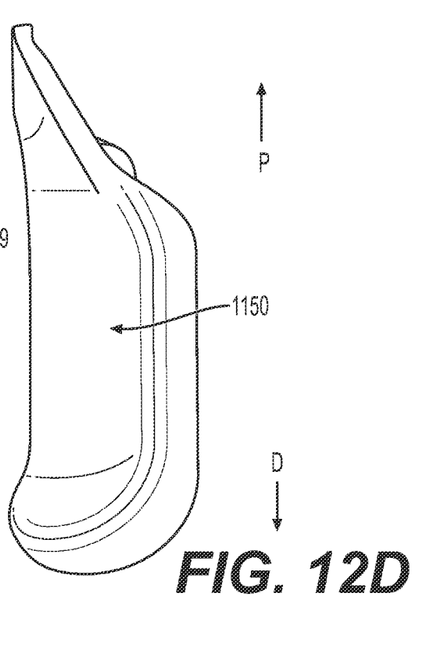

FIG. 11B shows a user's hand 201 holding handle assembly 106 and hand assist device 1150. The user may position accessory 1003 within opening 1154 of locking portion 1151 to temporary restrain movement of accessory 1003.

Hand assist devices 350, 1150 of the present disclosure may assist with supporting the palm and fingers of the user when the user operates endoscope 101 or other medical devices, and may reduce the chance of the user losing his or her grip. Also, the hand assist devices 350, 1150 may help prevent repeated repositioning of a user's hand on a medical device handle due to fatigue, strain, or other difficulty. Each of the aforementioned hand assist devices, whether used in conjunction with an endoscope system or any other medical device, may be used to enhance and/or facilitate a user's grip on a handle. Any of the hand assist devices discussed herein may be incorporated into a handle of an endoscope or other medical device such that the grip of the handle includes an exterior surface with a figure support portion, a palm support portion, and/or a base support portion similar to those discussed herein above. For example, the handle of an endoscope or other medical device can be molded or otherwise manufactured to have the contours and shapes of the exterior surfaces of the hand assist devices disclosed herein.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and embodiments be considered as exemplary only.

We claim:

1. A hand assist device configured for use with a medical device, the hand assist device comprising:
 a body configured to be removably coupled to a handle of the medical device, wherein the body comprises:
 a recess configured to receive the handle of the medical device,
 wherein the recess extends from a proximal end of the body to a distal end of the body;
 a palm support portion;
 a finger support portion proximal to the palm support portion; and
 a base support portion distal to the palm support portion,
 wherein a radially-inner surface of the body extends more than 180 degrees around a central longitudinal axis of the body, wherein the base support portion projects radially outward from the central longitudinal axis of the body relative to the palm support portion and includes a curved, concave exterior surface facing away from the central longitudinal axis.

2. The hand assist device of claim 1, wherein the base support portion extends radially outward, relative to the palm support portion, and is positioned at the distal end of the body.

3. The hand assist device of claim 1, wherein the finger support portion is disposed at the proximal end of the body and extends less than 180 degrees around the central longitudinal axis of the body.

4. The hand assist device of claim 1, further comprising a locking portion configured to receive an accessory device, wherein the locking portion is (i) C-shaped, (ii) spaced from the recess, and (iii) protrudes radially.

5. The hand assist device of claim 1, wherein the body defines a longitudinal opening between two longitudinal edges of the body, and wherein the longitudinal opening leads to the recess.

6. The hand assist device of claim 1, wherein the palm support portion is configured to fill a space between a palm and a handle body of the handle of the medical device, and includes a curved portion that protrudes radially outward from the central longitudinal axis of the body.

7. The hand assist device of claim 6, wherein the curved portion has an apex at a radially-outermost portion of the body.

8. The hand assist device of claim 1, wherein the finger support portion is configured to be positioned adjacent to at least one button of the handle of the medical device when the hand assist device is coupled to the medical device, and is configured to fill a space between an index finger and the handle of the medical device.

9. The hand assist device of claim 1, wherein the finger support portion is configured to be positioned proximate to, and distal, to an end portion of an umbilicus of the medical device when the hand assist device is coupled to the handle of the medical device.

10. The hand assist device of claim 1, wherein the base support portion is positioned at a distalmost end of the body.

11. The hand assist device of claim 1, wherein the body further comprises a surface protrusion configured to be positioned between a middle finger and a ring finger of a user, and wherein the surface protrusion is positioned between the palm support portion and the finger support portion.

12. The hand assist device of claim 1, wherein the palm support portion includes a radially-inward facing surface relative to the central longitudinal axis of the body, wherein the radially-inward facing surface extends circumferentially more than 180 degrees around the central longitudinal axis of the body.

13. The hand assist device of claim 1, wherein the body includes a flexible material such that the recess can be forced between an at-rest configuration and an enlarged configuration for receiving the medical device.

14. A hand assist device configured for use with a medical device, the hand assist device comprising:
   a body configured to be removably coupled to a handle of the medical device, wherein the body comprises:
      a recess configured to receive the handle of the medical device,
         wherein the recess extends from a proximal end of the body to a distal end of the body;
      a palm support portion;
      a finger support portion proximal to the palm support portion;
      a base support portion distal to the palm support portion, wherein a radially-inner surface of the body extends more than 180 degrees around a central longitudinal axis of the body; and
      a locking portion configured to receive an accessory device, wherein the locking portion is (i) C-shaped, (ii) spaced from the recess, and (iii) protrudes radially.

15. The hand assist device of claim 14, wherein the base support portion extends radially outward, relative to the palm support portion, and is positioned at the distal end of the body.

16. The hand assist device of claim 14, wherein the finger support portion is disposed at the proximal end of the body and extends less than 180 degrees around the central longitudinal axis of the body.

17. The hand assist device of claim 14, wherein the body defines a longitudinal opening between two longitudinal edges of the body, and wherein the longitudinal opening leads to the recess.

18. The hand assist device of claim 14, wherein the palm support portion is configured to fill a space between a palm and a handle body of the handle of the medical device, and includes a curved portion that protrudes radially outward from the central longitudinal axis of the body.

19. The hand assist device of claim 18, wherein the curved portion has an apex at a radially-outermost portion of the body.

20. The hand assist device of claim 14, wherein the finger support portion is configured to be positioned adjacent to at least one button of the handle of the medical device when the hand assist device is coupled to the medical device, and is configured to fill a space between an index finger and the handle of the medical device.

* * * * *